(12) United States Patent
McKenzie

(10) Patent No.: US 6,932,758 B1
(45) Date of Patent: Aug. 23, 2005

(54) COUPLED SEED TRAIN

(75) Inventor: Robert McKenzie, Tampa, FL (US)

(73) Assignee: Bruno Schmidt, Tampa, FL (US)

( * ) Notice: Subject to any disclaimer, the term of this patent is extended or adjusted under 35 U.S.C. 154(b) by 58 days.

(21) Appl. No.: 10/364,637

(22) Filed: Feb. 12, 2003

(51) Int. Cl.⁷ .............................................. A61N 5/00
(52) U.S. Cl. ........................................................ 600/8
(58) Field of Search ............................... 600/1–8, 585; 52/17.2, 108, 800.14, 786.13, 786.11, 786.1, 52/741.1, 788.1; 228/138; 606/28; 602/105

(56) References Cited

U.S. PATENT DOCUMENTS

| | | | | |
|---|---|---|---|---|
| 4,819,618 A | * | 4/1989 | Liprie | 600/7 |
| 5,133,710 A | * | 7/1992 | Carter et al. | 606/28 |
| 5,460,592 A | * | 10/1995 | Langton et al. | 600/7 |
| 6,010,446 A | * | 1/2000 | Grimm | 600/3 |
| 6,159,143 A | * | 12/2000 | Lennox | 600/4 |
| 6,264,600 B1 | * | 7/2001 | Grimm | 600/7 |
| 6,273,851 B1 | * | 8/2001 | Slater et al. | 600/8 |
| 6,497,647 B1 | * | 12/2002 | Tucker | 600/8 |
| 2004/0015037 A1 | * | 1/2004 | Rapach et al. | 600/1 |

* cited by examiner

Primary Examiner—Max F. Hindenburg
Assistant Examiner—Nikita R. Veniaminov
(74) Attorney, Agent, or Firm—Stanley M. Miller

(57) ABSTRACT

A coupled seed train is formed by placing a plurality of seed train members into the lumen of a hollow tube. A plurality of accommodation slots are formed in the tube in spaced relation to one another along the length of the hollow tube. The members of the seed train are positioned within the lumen such that each accommodation slot is in registration with a space between contiguous members of the seed train. An adhesive is introduced into each accommodation slot to join the members of the train to one another in end-to-end relation with one another. The seed train and plunger are then placed into the lumen of a needle and the needle is introduced into the tissue of a patient. A plunger abuts the trailing end of the seed train and remains stationary as the needle is withdrawn over the seed train and plunger. The seed train is deployed at the proper position within the tissue. The needle and the plunger are then withdrawn from the tissue.

13 Claims, 2 Drawing Sheets

COUPLED SEED TRAIN

BACKGROUND OF THE INVENTION

1. Field of the Invention

This invention relates, generally, to the medical field. More particularly, it relates to the field of brachytherapy.

2. Description of the Prior Art

In the field of brachytherapy, which relates to the placing of radioactive seeds and non-radioactive spacers in the prostate and other internal organs, it is advantageous to maintain the seeds and spacers of a seed train in alignment with one another after implantation. Loose seeds have a tendency to migrate a few millimeters after placement. If the seeds and spacers in the train are not coupled to one another, the seeds may move and turn within the prostate after implantation. If that happens, the seeds will be misaligned with one another when a radiograph is taken. The radiograph is important because every seed needs to be accounted for. If the seeds are in a straight line, they are easy to count. If they are jumbled, counting becomes more difficult.

A commercially available device, sold under the trademark Rapid Strands by Nycomed Amersham, uses suture material to encapsulate the members of the seed train. Moreover, there are various implantable tubes, strands, or other methods in the marketplace that encapsulate the seed/spacer train and that limit the movement of the seeds relative to one another.

However, the known techniques are somewhat expensive and some of the known techniques do not reliably couple the members of a seed train to one another.

What is needed, then, is a low cost and highly effective way of coupling together the members of a seed train.

However, in view of the prior art considered as a whole at the time the present invention was made, it was not obvious to those of ordinary skill in the pertinent art how these needs could be fulfilled.

SUMMARY OF THE INVENTION

The long-standing but heretofore unfulfilled need for an improved method of coupling the members of a seed train to one another in end-to-end relation is now provided by a new, useful, and nonobvious invention. The novel method includes the steps of positioning a plurality of members of a seed train in spaced apart, end-to-end alignment with one another. A biocompatible adhesive is applied in a space between a trailing end of a first member and a leading end of a second member so that the adhesive adheres to the trailing end and the leading end of the members, respectively, thereby coupling the members in end-to-end alignment with one another.

The step of applying the adhesive is repeated for each space in the seed train, thereby forming an elongate seed train where contiguous members of the seed train are coupled to one another with the biocompatible adhesive at their respective leading and trailing ends.

The step of applying the adhesive in each space between seed members is significantly facilitated by providing a hollow tube. A plurality of applicator slots are formed in the hollow tube at spaced intervals along its length. The plurality of members of the seed train are positioned in spaced apart, end-to-end alignment with one another within a lumen of the hollow tube such that each applicator slot in the hollow tube is in registration with a space between seed train members.

The adhesive, preferably a member of the methacrylate group, such as methyl-methacrylate or butyl-methacrylate, is preferably applied in the form of a fine spray through each of the applicator slots to join contiguous members of the seed train to one another. The adhesive may be dried with a heat gun to promote curing.

The steps of applying adhesive in the form of a fine spray and drying the adhesive with a heat gun may need to be repeated at least once to ensure solid coupling of the seeds and spacers to one another.

Contiguous seed train members may also be glued to one another by making a fixture or tube with one hole formed therein. Glue is dabbed onto the joints as the seed train is pushed through the tube. An opening is formed in the end of the fixture and heat from a heat source is directed through said opening to facilitate drying of the glue. The tube or fixture is made of Teflon® or other non-stick material.

The hollow tube is made of a material to which the adhesive does not adhere.

The seed train is ejected from the lumen of the hollow tube after the adhesive has cured.

A needle having a lumen with a diameter at least slightly larger than a diameter of the seed train is provided and the seed train is slideably positioned within the lumen of the needle.

The needle is introduced into tissue, and a plunger is slideably inserted into the lumen of the needle so that a leading end of the plunger (stylet) abuts a trailing end of the seed train. The needle is withdrawn while the position of the plunger is maintained. The plunger and needle are withdrawn together thereby leaving the seed train in a preselected position within the tissue.

A bioabsorbable adhesive may be employed so that the bioabsorbable adhesive is bioabsorbed over time, leaving the members of the seed train in alignment with one another.

Bioabsorbable spacers may also be employed so that the bioabsorbable spacers are bioabsorbed over time, leaving the seeds of the seed train in alignment with one another.

The novel apparatus for performing the steps of the novel method is thus understood to include a hollow tube and a plurality of applicator slots formed in the hollow tube at spaced intervals along the length of the hollow tube. A plurality of members of the seed train are disposed in spaced apart, end-to-end alignment with one another within a lumen of the hollow tube such that each applicator slot in the hollow tube is in registration with a space between seed train members. The apparatur includes means for applying an adhesive through each of said applicator slots to join contiguous members of the seed train to one another.

An alternate apparatus for joining together contiguous members of a seed train includes an elongate fixture. A seed and spacer loading area is positioned at a first end of the fixture and a glue area is disposed in longitudinally spaced relation to the seed and spacer load area. An opening is formed in the glue area and is adapted to receive glue therethrough. The glue area is disposed transversely to a longitudinal axis of the elongate fixture. A drying area is disposed in longitudinally spaced relation to the glue area and a needle housing connector area is disposed in longitudinally spaced relation to the drying area at a second end of the fixture.

An important object of this invention is to provide an effective and reliable way of coupling together the members of a seed train in end-to-end alignment with one another.

A closely related object is to accomplish the foregoing object in a cost-effective way.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawing, in which.

DETAILED DESCRIPTION OF THE PREFERRED EMBODIMENT

Figure 1:
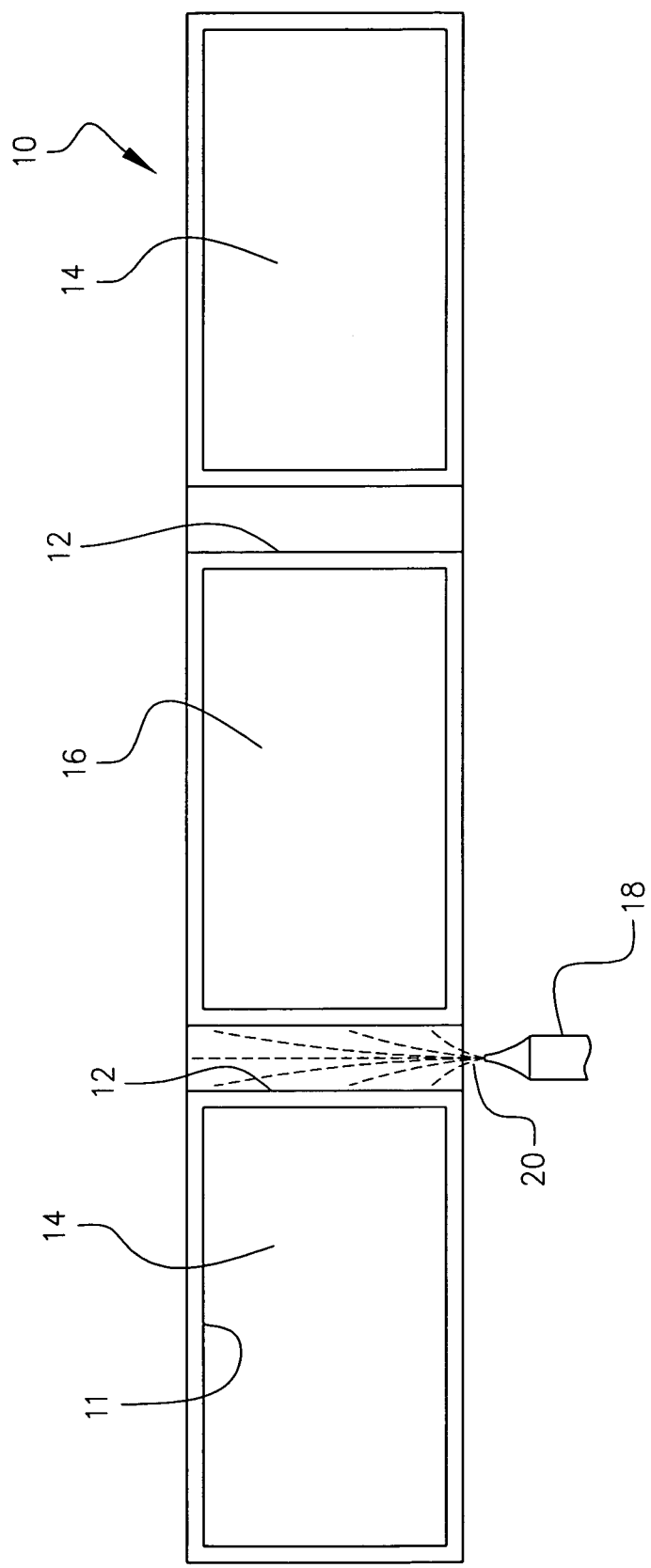
FIG. 1 is a side elevational view of a fixture employed in the novel method.

Referring to FIG. 1, it will there be seen that the reference numeral 10 denotes an illustrative embodiment of the present invention as a whole.

More specifically, reference numeral 10 denotes a hollow tube having a plurality of accommodation slots, collectively denoted 12, formed therein along its length in longitudinally spaced relation to one another. The lumen of tube 10 is denoted 11.

In this illustrative embodiment, and viewing the Figure from left-to-right, seed 14 is followed by spacer 16 and spacer 16 is followed by another seed 14. It should be understood, however, that hollow tube 10 can accommodate large numbers of seeds and spacers and that short tube 10 holding only three of such seed and spacer members is depicted for discussion purposes only.

It should also be understood that the arrangement of seeds and spacer inside lumen 11 need not be in the alternating (seed-spacer-seed) configuration of the Figure. A physician may arrange seeds 14 and spacers 16 in any combination, depending upon the location, size, and shape of a tumor or tumors within the prostate or other internal organ. Thus, the arrangement may take the form of seed-spacer-spacer-seed-seed-seed-spacer, and so on. For purposes of discussion, all seed-spacer arrangements are collectively referred to herein as a "seed train." Again, it should be understood that the term "seed train" includes seeds and spacers as well, in any arrangement. For simplicity purposes, seeds and spacers are referred to herein as "members" of a seed train.

The first step of the novel method is to provide hollow tube 10 having a plurality of accommodation slots 12 formed therein in longitudinally spaced relation to one another.

The second step is to arrange a seed train therein in such a way that the space between each member of the seed train is in registration with an accommodation slot 12, as depicted in the Figure.

The third step is to apply a biocompatible adhesive between each member of the seed train to thereby join them together. In a preferred embodiment, the adhesive is applied in a fine spray by a spray gun 18 that is positioned in registration with an accommodation slot 12 when the adhesive is applied. The adhesive is denoted by the reference numeral 20.

A filler may be added to the adhesive so that the adhesive may also act as a spacer. This enables variability of spacing between the seeds. The spacing is determined by the amount of filled adhesive that is deposited between the seeds.

It is advantageous to promote curing of the adhesive after application by heating it. In a preferred embodiment, a heat gun is employed to direct heat onto the adhesive after it has been sprayed into the space between the members of the seed train. To ensure a good joint, it may be necessary to apply a fine spray of adhesive, heat the adhesive with the heat gun to cure the adhesive, and to repeat the spraying and heating process one or more times until a good joint is assured. Adhesive may also be applied to the joint by daubing or some other suitable method.

Although the heat gun is not uniquely depicted, the Figure may be interpreted by letting the reference numeral 18 also denote said heat gun. When so interpreted, the heat radiated by said gun is denoted by the reference numeral 20. Thus, the reference numeral 18 can be understood as depicting both a sprayer 18 for adhesive 20 and as a heat gun 18 for radiating heat 20. Of course, as already made clear, said sprayer is used first, followed by said heat gun.

Hollow tube 10 is preferably formed of Teflon® or other non-stick material so that the adhesive does not adhere to said hollow tube.

By adding a filler to the adhesive, the adhesive may also act as a spacer, thereby enabling variability of spacing between the seeds. The spacing is determined by the amount of filled adhesive that is deposited between the seeds.

The fourth step of the novel method is to eject the seed train, with all of its contiguous members securely adhered to one another, from hollow tube 10.

The remaining steps are conventional. The seed train, having been removed from the lumen of hollow tube 10, is slideably inserted into the lumen of a brachytherapy needle, not shown.

The brachytherapy needle is inserted into the patient's tissue at a location determined by a physician, and a plunger is slideably inserted into the lumen of the needle from the exposed trailing end thereof. The leading end of the plunger is placed against the trailing end of the trailing member of the seed train and the needle is withdrawn while the position of the plunger is maintained. The needle is then withdrawn, leaving the seed train in the tissue.

If a bioabsorbable adhesive is used, such adhesive will become bioabsorbed gradually over time. Thus, the members of the seed train will still be adhered to one another and therefore in alignment with one another when a radiograph is taken after the completion of the procedure. However, since the adhesive is biocompatible, it need not be bioabsorbable.

The same observation applies to the seeds, i.e., they may or may not be bioabsorbable because they are biocompatible. If they are bioabsorbable, they will remain unabsorbed for a period of time sufficient to take the aforementioned radiograph.

This novel method does not rely upon encapsulaton of the members of a seed train by suture material or other means and as such represents a significant advance in the art. The novel hollow tube having spaced apart accommodation slots facilitates the performance of the steps of the method, although it is possible to adhere contiguous members of a seed train together without using said hollow tube. Nor must accommodation slots 12 be equidistantly spaced from one another because there may be an application where the members of the seed train are of differing lengths and such would require that the accommodation slots be spaced as needed.

Figure 2:
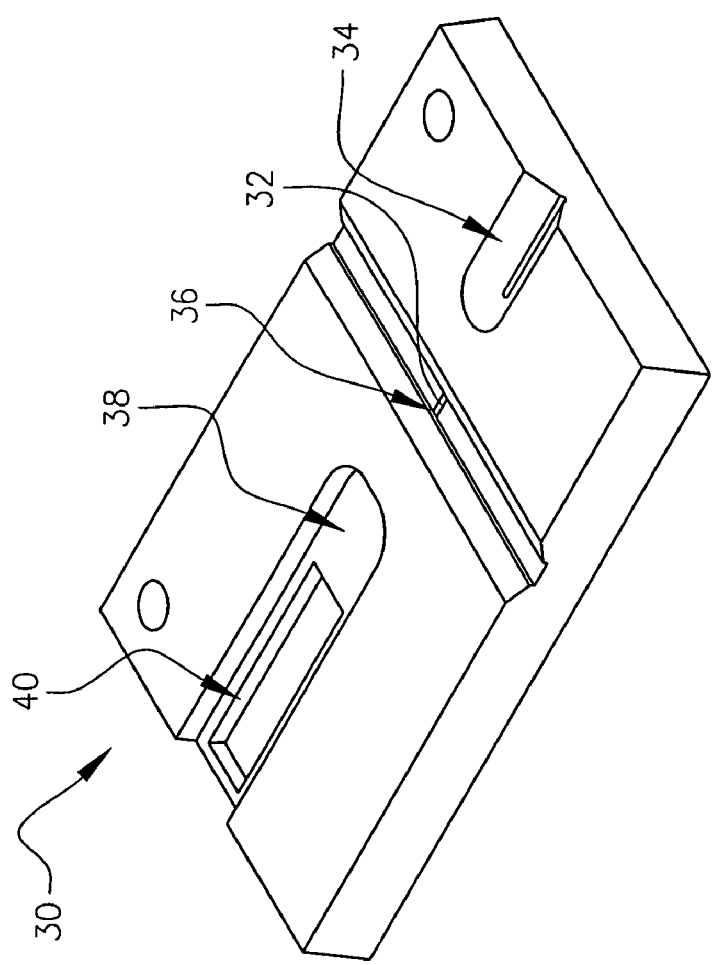
FIG. 2 is a perspective view of an alternative method for gluing together contiguous members of the seed train.

FIG. 2 depicts an alternative apparatus for gluing contiguous seed train members to one another. Elongate fixture 30 has one opening 32 formed therein. Glue is dabbed onto the joints through said opening 32 as the seed train is pushed through the fixture. More particularly, the seeds and spacers are loaded into elongate fixture 30 at seed and spacer load area 34 which is formed in said fixture at a first end thereof. The seeds and spacers are then pushed to glue area 36 in the middle of which is said hole 32. Glue area 32 is longitudinally spaced from seed and spacer load area 34 and is transversely disposed with respect to the longitudinal axis of elongate fixture 30. The seeds and spacers then enter into drying area 38 which is longitudinally spaced from glue area 36. After drying they are pushed to needle housing connector area 40 which is disposed at a second end of said elongate fixture and which is longitudinally spaced from drying area 38. Elongate fixture 30 is made of Teflon® or other non-stick material.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A method for coupling together the members of a seed train, comprising the steps of:

positioning a plurality of members of a seed train in spaced apart, end-to-end alignment with one another;

applying a biocompatible adhesive to a spade between a trailing end of a first member and a leading end of a second member so that the biocompatible adhesive adheres to said trailing end and said leading end of said first and second members, respectively, thereby coupling said members in end-to-end alignment with one another when said adhesives cures;

repeating said step in each space in said seed train, thereby forming an elongate seed train by adhering contiguous members of said seed train to one another with said biocompatible adhesive at their respective leading and trailing ends;

providing a hollow tube;

forming a plurality of applicator slots in said hollow tube at spaced intervals along the length of said hollow tube;

positioning said plurality of members of said seed train in spaced apart, end-to-end alignment with one another within a lumen of said hollow tube such that each applicator slot in said hollow tube is in registration with a space between seed train members;

applying said adhesive through each of said applicator slots to join contiguous members of said seed train to one another;

said step of applying said adhesive including the step of applying said adhesive in the form of a fine spray.

2. The method of claim 1, wherein said step of applying said adhesive includes the step of applying said adhesive by daubing in lieu of said fine spray.

3. The method of claim 1, wherein said hollow tube is made of a material to which said adhesive does not adhere.

4. The method of claim 1, further comprising the step of:

ejecting said seed train from said lumen of said hollow tube after said adhesive has cured.

5. The method of claim 4, further comprising the steps of:

providing a needle having a lumen with a diameter at least slightly larger than a diameter of said seed train; and slideably positioning said seed train within said lumen of said needle.

6. The method of claim 5, further comprising the step of:

slideably inserting a plunger into said lumen of said needle so that a leading end of said plunger abuts a trailing end of said seed train;

introducing said needle into tissue;

withdrawing said needle while maintaining the position of said plunger relative to the patient, until the seed train is deployed; and withdrawing said needle and plunger together after deployment of the seed train.

7. The method of claim 1, further comprising the step of employing a bioabsorbable adhesive so that said bioabsorbable adhesive is bioabsorbed over time, leaving said members of said seed train in alignment with one another.

8. The method of claim 1, further comprising the step of employing bioabsorbable spacers so that said bioabsorbable spacers are bioabsorbed over time, leaving said seeds in alignment with one another.

9. The method of claim 1, wherein the adhesive is a member of the methacrylate group.

10. The method of claim 1, further comprising the step of drying said adhesive with a heat gun to promote curing of said adhesive.

11. The method of claim 10, wherein the steps of applying the adhesive and drying said adhesive with a heat gun are repeated at least once to ensure solid coupling of said seed and spacer to one another.

12. The method of claim 1, further comprising the step of adding a filler to the adhesive so that the adhesive also acts as a spacer, thereby enabling variability of spacing between the seeds, said spacing being determined by the amount of filled adhesive that is deposited between the seeds.

13. The method of claim 1, wherein the applicator slots are equidistantly spaced apart from one another.

* * * * *